United States Patent [19]

L'Esperance

[11] Patent Number: 4,580,559
[45] Date of Patent: Apr. 8, 1986

[54] INDIRECT OPHTHALMOSCOPIC PHOTOCOAGULATION DELIVERY SYSTEM FOR RETINAL SURGERY

[76] Inventor: Francis A. L'Esperance, 255 Oakwood Rd., Englewood, N.J. 07631

[21] Appl. No.: 633,903

[22] Filed: Jul. 24, 1984

[51] Int. Cl.⁴ .............................................. A61B 17/36
[52] U.S. Cl. ................. 128/303.1; 128/395; 128/645; 350/96.18; 351/217
[58] Field of Search ..................... 128/303.1, 395, 645; 350/96.18; 351/217

[56] References Cited

U.S. PATENT DOCUMENTS

| | | | |
|---|---|---|---|
| 1,806,318 | 5/1931 | Tillyer | 351/217 |
| 3,783,874 | 1/1974 | Koester et al. | 128/303.1 |
| 3,910,276 | 10/1975 | Polanyi et al. | 128/303.1 |
| 3,930,504 | 1/1976 | De Laforcade | 128/303.1 |
| 4,125,320 | 11/1978 | Rassow et al. | 351/217 |
| 4,170,997 | 10/1979 | Pinnow et al. | 128/395 |
| 4,313,093 | 1/1982 | Suenega et al. | 128/303.1 |
| 4,391,275 | 7/1983 | Fankhauser et al. | 128/303.1 |
| 4,397,310 | 8/1983 | Pomerantzeff | 128/303.1 |
| 4,408,602 | 10/1983 | Nakajima | 128/303.1 |
| 4,421,382 | 12/1983 | Doi et al. | 128/303.1 |
| 4,499,897 | 2/1985 | Roussel | 128/395 |
| 4,520,816 | 6/1985 | Schachar et al. | 128/395 |
| 4,520,824 | 6/1985 | Swaniger et al. | 128/395 |

FOREIGN PATENT DOCUMENTS 2611933  9/1977  Fed. Rep. of Germany ... 128/303.1

OTHER PUBLICATIONS

L'Esperance, "Chapter 2-Laser Sources and Ocular Effects", *Ophthalmic Lasers*, 2nd Ed., C. V. Mosby Co., St. Louis, 1983, pp. 8-27.
Liben et al., "An Argon Laser Photocoagulator", *APL Technical Digest*, vol. 11, No. 3, (Jan.-Feb. 1972), pp. 2-14.
Taboada et al., "Response of the Corneal Epitheuum to KrF Excimer Laser Pulses", *Health Physics*, v. 40, May 1981, pp. 677-683.

*Primary Examiner*—John Doll
*Assistant Examiner*—Lance Johnson
*Attorney, Agent, or Firm*—Hopgood, Calimafde, Kalil, Blaustein & Judlowe

[57] ABSTRACT

In a preferred embodiment, a portable ophthalmoscope having low-power telescope elements and having an internal source of viewed-field illumination, relies on a patient's focusing properties to inspect the fundus of the eye. A laser-beam source is flexibly coupled to the patient end of the ophthalmoscope viewing axis and, after optical expansion and collimation, is folded into coincidence with the ophthalmoscope axis. A dichroic (filter) is the mirror via which the folding takes place, the filter being selected for a very narrowly limited spectral band of great attenuation of radiation at the characteristic wavelength of the involved laser, the latter having been selected for its photocoagulating and/or photoablating action on locally afflicted tissues of the retinal, choroid and/or other internal regions of the eye.

19 Claims, 7 Drawing Figures

INDIRECT OPHTHALMOSCOPIC PHOTOCOAGULATION DELIVERY SYSTEM FOR RETINAL SURGERY

BACKGROUND OF THE INVENTION

The invention relates to laser surgery and in particular to apparatus which is sufficiently portable to enable manual manipulation of laser radiation in the performance of a surgical operation at a predetermined point or points in the choroid, retina or other internal areas of an afflicted eye.

Laser surgery to date within the eye has involved relatively bulky apparatus wherein a slit lamp is the surgeon's means of observing the fundus of the patient's eye, and the output of a laser is so folded onto the axis of slit-lamp observation as to focus a desired laser-beam spot at the fundus. This necessarily involves use of the focusing power of the eye, and a lens system in external contact with the cornea is employed to correct astigmatic and other refractive errors, so as to control fidelity and size of the laser-beam spot at the fundus. With such apparatus, the slit lamp is desk-mounted and the patient must sit upright, effectively clamping himself to the chin rest of the slit lamp, to assure his immobility. The slit lamp has certain degrees of aspect manipulation by the surgeon, and an auxiliary light source, such as the attenuated output of helium-neon laser is spliced into a collimated part of the laser-beam optical system (prior to folding into slit-lamp viewing axis), to provide a viewable spot which is the spot size of the laser beam relied upon for surgery; such an auxiliary light source and splicing are described in my copending application, Ser. No. 617,931, filed June 6, 1984.

Laser surgery to date within the eye has involved relatively bulky ruby, argon, krypton, neodymium-YAG, and organic dye lasers which, with conversion of light to heat energy, produce a thermal rise in tissue temperature sufficient to create a photocoagulation or coagulum. The pulsed neodymium-YAG laser, equally bulky, produces a moderate output power and short exposure which create high power densities; and the part of a body to be operated upon must be precisely positioned for the particular desired operation. Radiation wavelengths of the aforementioned lasers are in the visible or near-infrared portions of the spectrum and therefore local coagulation, vaporization, or disruption of tissue is a necessary consequent of the exposure. Careful alignment and assured fixation of the patient's eye are required, for each laser exposure. When the infirmity requires several exposures, as at different locations on the retina, the procedure is cumbersome and time-consuming, requiring great patient cooperation, and the apparatus is very expensive.

In my copending application Ser. No. 552,983, filed Nov. 17, 1983, I disclose laser apparatus and techniques for ophthalmological surgery wherein selective ablation of body cells is achieved by photodecomposition, without coagulation or vaporization, using radiation in near end and far portions of the ultraviolet end of the spectrum; and in my copending applications, Ser. No. 571,827, filed Jan. 19, 1984 and Ser. No. 617,931, filed June 6, 1984, I disclose further such apparatus having ophthalmological application, the device of Ser. No. 571,827 being a pencil-like manipulable tool with flexible optical-fiber cable connection to a local source of laser radiation, and the device of Ser. No. 617,931 being a scanning laser apparatus for non-invasively removing a cataractous lens. Reference is made to said applications for more complete discussion.

BRIEF STATEMENT OF THE INVENTION

It is an object of the invention to provide improved laser apparatus for surgically treating the choroid, retina, or other internal structures of the eye.

A specific object is to meet the above object with a light-weight portable apparatus wherein an illuminated field of view as of the retina, is continuously viewable, with a viewed indication of the size and instantaneous location at which photocoagulating laser radiation can be made to impinge, as the surgeon may determine and control.

Another specific object is to provide such apparatus with the ability to non-invasively operate and to view the progress of a photocoagulating operation upon a precisely observed point or points of a given retina.

It is also an object to provide the surgeon with easily adjusted means whereby he can view his adjustment of the spot size, which will be the laser spot size, within his field of observation.

A further specific object is to provide such laser-surgery capability as an add-on feature of a conventional indirect ophthalmoscope.

It is a general object to meet the above objects with essentially simple structure, featuring precision and ease of use.

In a preferred embodiment, the invention achieves these objects using an indirect ophthalmoscope having a low-power afocal telescope which relies on optical properties of the patient's focusing ability to enable inspection of the fundus of the eye, an internal light source of the ophthalmoscope being projected along the telescope axis to illuminate a field of view within which an operation is to be performed. Fixedly carried by the telescope is the output end of an optical-fiber cable providing flexible connection to the output of a local laser-beam source, and a beam-splitter (preferably a dichroic mirror) in conjunction with beam-shaping optical elements folds laser energy precisely onto the telescope axis. The observed field of view displays a "center" indicium whereby the surgeon can know where the laser spot will impinge the retina within the observed field, once the surgeon decides to trigger the release of laser energy, and the surgeon can safely observe the progress of a photocoagulating operation upon his selected spot or spots in the fundus.

DETAILED DESCRIPTION

The invention will be illustratively described in detail, in conjunction with the accompanying drawings, in which.

Figure 1:
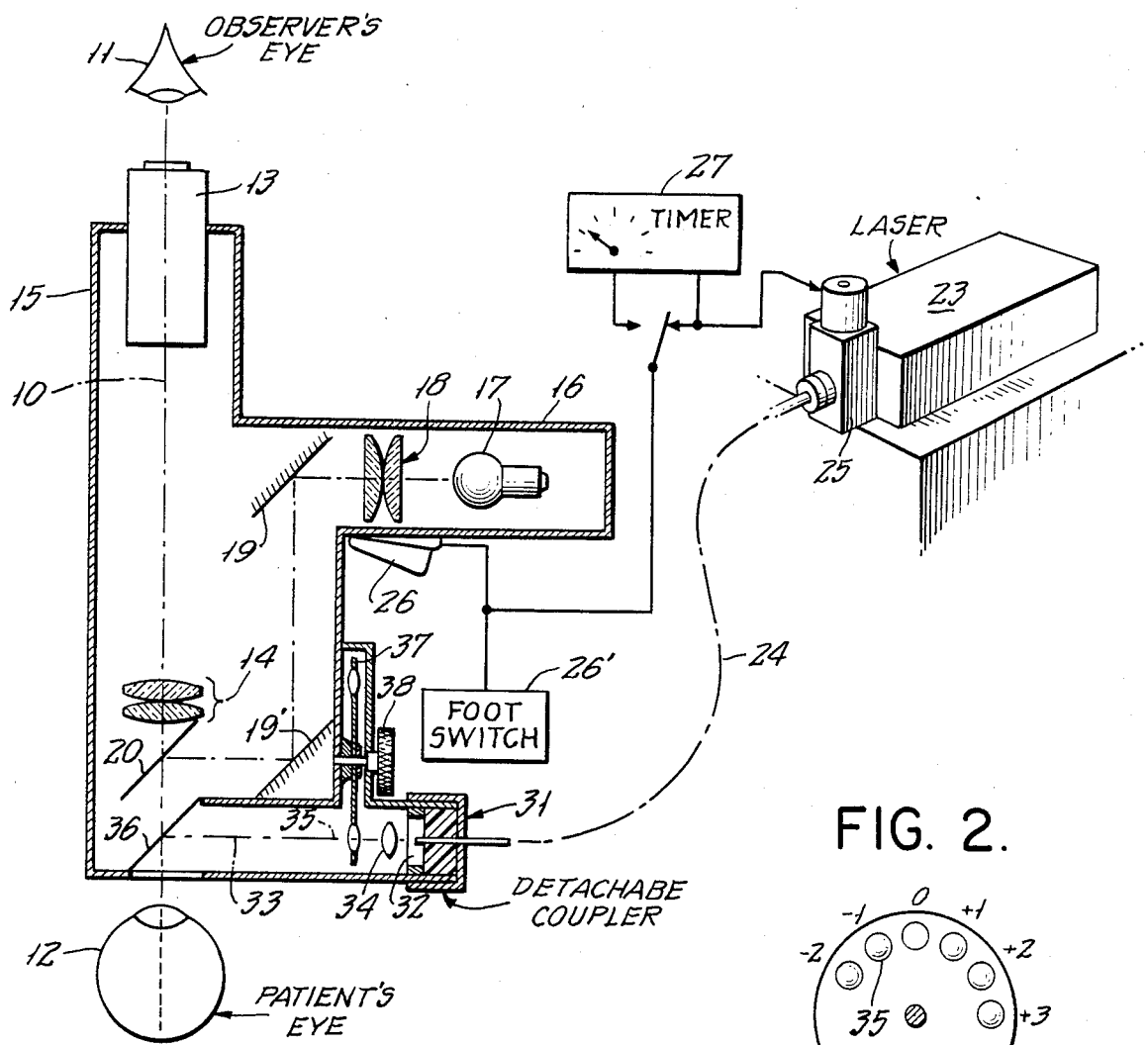
FIG. 1 is a simplified and somewhat schematic view of a photocogulation delivery system of the invention.

The photocoagulation delivery system of FIG. 1 comprises a light-weight portable indirect ophthalmoscope or afocal telescope having a viewing axis 10 which is shown extending from the observing surgeon's eye 11 to and through refractive media of the patient's eye 12 for focus at the fundus of the eye. For portability, the ophthalmoscope is preferably monocular, and it is shown to comprise ocular means 13 and objective means 14, selected to use the focusing ability of eye 12 and to provide relatively low power magnification of a field of view at the fundus. The optical means 13-14 will be understood to be carried by a suitable housing 15, with customary provision for focal adjustment, i.e., for suitably sharp observation at least at the instantaneous center of the observed field; more specifically, the ocular means 13 will be understood to include provision (not shown) for adjustable focus, to enable refractive errors of the patient and of the observing physician to be neutralized. Within a hand-grip portion 16 of the housing, extending in one direction of generally radially projecting offset from the axis 10, a lamp 17 provides an internal source of illumination of the instantaneous field of view, relying upon a lens system 18, folding mirrors 19—19' and a beam splitter 20 to merge the illumination axis with the view axis 10; the illuminating rays come to a focus at the plane of the patient's pupil and then diverge, illuminating the vitreous, the choroid and the retina. The image of the choroid and retina similarly is emergent through the pupillary plane, and the light rays thereof are captured by the objective means 14, establishing the aerial real image within the telescope. The parts thus far described are all contained in a hand-held monocular ophthalmoscope, identifiable as the "Wide-30", being a commercial (Nikon) product of Nippon Kogaku K.K., Tokyo, Japan, and reference is made to pertinent Nikon literature for more detailed description.

Figure 3:
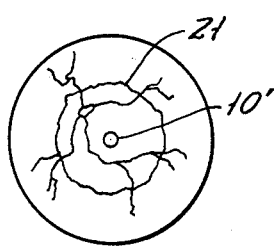
FIGS. 3 and 4 are diagrams to illustrate field of viewing a retina in use of the system of FIG. 1, FIG. 4 involving a slight modification from FIG. 3.
Figure 4:
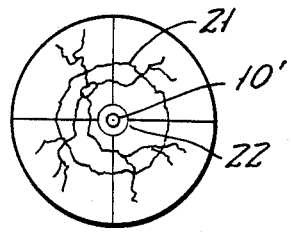

FIG. 3 depicts an illustrative view by the observer's eye 11, wherein illuminating flux from lamp 17 is uniformly impinged upon and within a retinal area 21 which is generally circular and which is centered upon the instantaneous alignment of axis 10, the latter being identified in FIG. 3 as a small centered spot 10' within the illuminated field 21. In some circumstances, a reticule having a center-locating ring 22 may be incorporated in the telescope system whereby ring 22 is at all times viewed around the center of the currently viewed field (see FIG. 4).

Figure 2:
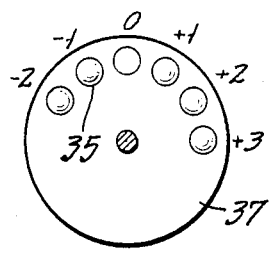
FIG. 2 is a plan view of a part in the system of FIG. 1.
Figure 2A:
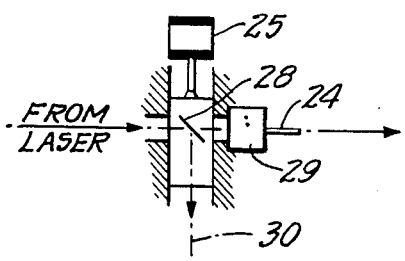
FIG. 2A is a simplified fragmentary diagram to illustrate a shutter mechanism in the system of FIG. 1.

In accordance with a feature of the invention, the beam of a suitable laser 23 is so coupled by a flexible optical-fiber cable 24 to auxiliary optical means carried by housing 15 as to deliver at the fundus of eye 12 a photocoagulating beam of viewable spot size represented at 10' in FIG. 3. The delivery system of FIG. 1 includes a solenoid-operated shutter 25 under optional control of a trigger switch 26 or a foot switch 26', and optionally with or without a timer 27 of preselected time. In FIG. 2A, shutter 25 will be seen to comprise a slide-mounted neutral-density beam splitter 28, inclined at 45 degrees to the axis of laser output and delivery to cable 24, delivery being via a coupler 29. In the normal or unactuated state shown, the shutter is "closed", deflecting most of the energy of laser output along a lateral axis 30, as to a power-metering or other absorbing device (not shown), only a small fraction of the energy being passed to cable 24 for delivery at 10' in the illuminated field. In the actuated state of shutter 25, its solenoid will have elevated the slide mount for splitter 28, thus eliminating beam deflection and delivering full laser-beam output to cable 24 via coupler 29.

At a side port of housing 15, cable 24 is shown to be fixedly carried by and to terminate at detachable coupler means 31, so configured with respect to a fixed annular stop 32 (forming part of housing 15) as to precisely position the delivery end of cable fiber on the axis 33 of optical elements 34 and 35. Emergent rays that are divergent from the fiber of cable 24 are captured by the biconvex lens 34, which will be understood to be so positioned with respect to the output end of the optical fiber as to project a collimated beam of enlarged section which, after folding at 36 is responsible for the spot 10' in the illuminated field of view. Suitably, the collimated beam attributable to lens 34 is of approximately 2-mm diameter.

The optical element 35 is one of a plurality of such elements, of progressively different dioptric power, for selective manipulative indexing into the collimated beam developed by lens 34. As seen in FIG. 2, these elements are circumferentially arrayed in angularly spaced relation on a disc or wheel 37; and lens 35 is at the "−1" location, meaning that a correction of −1 dpt is needed, in the context of correction needed for the refractive power of the patient's eye, to establish the desired diameter of spot 10'. Wheel 37 is shaft-mounted to housing 15, with an external knob 38 for indexing manipulation, while observing the field 21. In this manner, the surgeon can not only observe the progressive correction of spot 10' to adapt to an error of the refractive power of eye 12, but he can also have a measure of selective control of the spot size he deems best at 10' for a particular job.

The folding device 36 is a beam splitter, and preferably a dichroic mirror, selected for its ability to reflect essentially only a narrow band of the visible spectrum, the narrow band being selected to include the characteristic wavelength of the output of laser 23; outside this narrow band of reflection wavelengths, the dichroic mirror passes remaining components of the visible spectrum. Such dichroic mirrors are also known as dichroic filters; they reflect (at a very narrow band) approximately 90 percent of the incident laser light. Thus, for a frequency-doubled neodymium-YAG laser at 23, the very narrow band of reflection of a "532-nm" dichroic filter will include 90 percent of the characteristic 532-nm (green) radiation of the laser, and visible light on the blue and red sides of the narrow band will be transmitted, along with the remaining 10 percent of the laser light. Dichroic mirrors (filters) of the character indicated are available from Optical Coating Laboratory, Inc., Santa Rosa, Calif.

Figure 5:
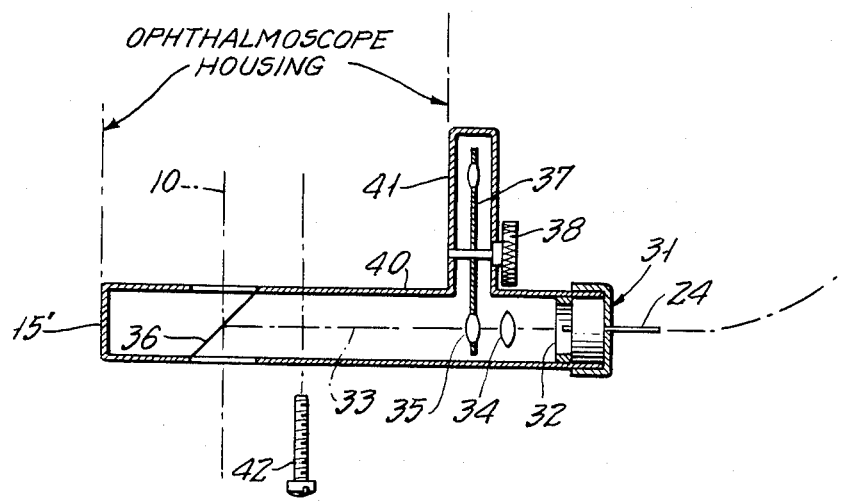
FIGS. 5 and 6 are views similar to FIG. 1 to illustrate other embodiments.

FIG. 5 illustrates a kit component whereby a standard portable ophthalmoscope, of the type described and referred to in connection with FIG. 1, may be converted or supplemented to enable viewed delivery of photocoagulating laser energy in the manner described in connection with FIG. 1. The kit component of FIG. 5 comprises a housing 15' configured for optically aligned fit to the delivery (patient's) end of the ophthalmoscope housing, the latter being only in partial phantom outline and designated by legend in FIG. 5. The component housing 15 includes an upper panel 40 and a contiguous upstanding panel 41 which will be understood to be configured to define a cove or concavity having precise fit to the similarly configured convex exterior of the ophthalmoscope housing, and an inserted relatively long bolt or bolts 42 (e.g., replacing the short bolt which retains the removable covering cup or plate at the patient's end of the ophthalmoscope housing) is all that is needed to secure the component of FIG. 5 in place, with mirror (filter) 36 aligned to reflect narrow-band laser light precisely into coincidence with the ophthalmoscope axis 10; it will be understood that for such coincidence, the axis 33 of laser light projection must intersect viewing axis 10, and that the normal to the reflecting surface must bisect the included angle between these intersecting axes. Once assembled to the ophthalmoscope, the laser-delivery component of FIG. 5 performs as described for the optical laser-delivery parts of FIG. 1; the same internal parts are therefore identified by the same reference numbers in FIG. 5.

Figure 6:
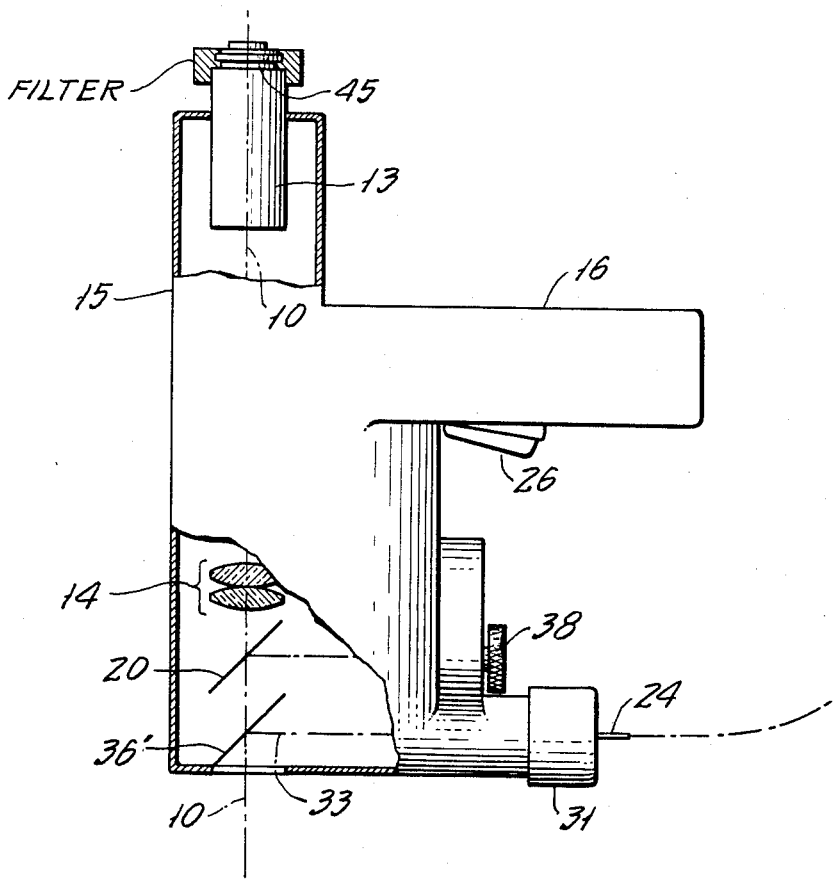

The delivery system of FIG. 6 will be recognized for its general conformance to the of FIG. 1, the only significant difference being that in FIG. 6, the dichroic mirror (filter) 36 of FIG. 1 has been replaced by a beam splitter 36' and a narrow-band filter 45 has been placed over the ocular 13 to protect the viewer's eyes from intense radiation at the laser wavelength. Thus, for the case of the illustrative 532-nm laser at 23, the filter 45 should be selected for substantial attenuation at this wavelength.

The described invention will be seen to achieve all stated objects. The various retinal afflictions that can be treated by pin-pointed photocoagulation with the described apparatus include diabetic retinopathy, Eales' disease and Coats' disease (Leber's retinopathy), macular degeneration, retinal tears, peripheral retinal degeneration, and retinal and choroidal tumors. But the surgeon may determine that different sizes of spot 10' are desired for particular afflictions within the indicated variety, so that it is a matter of real convenience and help to the surgeon that, merely by imparting indexing rotation to knob 38, he can see the actual context of laser-beam spot size and placement in the illuminated field 21; for example, for a wheel 37 accommodating ten lenses, in 1-dpt increments on each side of a zero-diopter position, spot size at 10' can be selected in the range from 30 microns to 1,000 microns, even for individuals with high degrees of myopia or hyperopia.

The physician has his choice, whether to time a given exposure himself, using only the trigger 26 or the footswitch, or to rely on his setting of timer 27. In the former case, he can observe photocoagulation taking place and terminate the same when he judges that the desired photocoagulation is sufficiently complete at a given treatment spot. In the latter case, he can select the time interval (e.g., 0.02 second to 5.0 seconds, selected at 27) over which laser exposure will apply for a given actuation of one or the other of switches 26—26'.

It has been indicated that photocoagulation is the result of 532-nm exposure, namely for the output of a frequency-doubled YAG laser. Photocoagulation also applies to differing extents at the characteristic wavelengths of other lasers in the visible spectrum, with increasing photoablation as such wavelengths are shorter, i.e., in the blue end of the spectrum. For example, by using an argon laser, the physician has an available supply of radiation at both of the characteristic 488-nm and 514-nm lines; he may opt to use both of these lines in which case his dichroic filter 36 (or his ocular filter 45) is selected to reflect a narrow band including both of these lines, in which case of course the viewable color observed via ocular 13 will be very unreal (being a mix of visible spectrum on the upper side of the 514-nm line, with visible spectrum on the lower side of the 488-nm line. If he opts to use either one, to the exclusion of the other of these argon lines, he should select his filter (36 or 45) to be as very narrowly limited as possible to the selected argon-characteristic wavelength line, thus affording least possible color distortion of the viewed image of the field. Still further, if the physician opts for photocoagulation with greater penetration of a moderately blood-filled eye, he may work with a krypton laser at 23, in which case filter action at 36 or 45 should be in a very narrow band which includes 647.1-nm.

In use of any of the described devices, it is found convenient to have the patient lie flat, face up, at such elevation as to permit the physician to be seated and to use his hands for steadying reference of the delivery instrument in desired orientation of downwardly directed delivery and observation.

While the invention has been described in detail for preferred embodiments, it will be understood that modification may be made without departing from the scope of the invention. For example, there are some who might prefer to use a binocular ophthalmoscope instead of the monocular system currently preferred. There is no reason why this cannot be done, but the apparatus becomes more bulky and much more expensive than the monocular system, and ease of portable manipulation is considerably diminished.

What is claimed is:

1. A portable indirect photocoagulation delivery system, comprising in combination, a hand-held ophthalmoscope including a low-power afocal telescope comprising a housing and optical elements that can be focused in the interior of an inspected eye, a light source carried by said housing and means including a beam splitter on the telescope axis for projecting light over an illuminated central field region in the interior of the inspected eye; laser means having a radiation-beam output, means including an elongate flexible optical-fiber cable coupled at one end to said output, said housing having a side port and retaining the other end of said cable through said side port and directing cable output on a laser-radiation axis within said housing, means including a dichroic mirror carried by said housing and in the path of telescope viewing, optical means on the laser-radiation axis directing said laser-radiation axis to intersect the telescope axis at said dichroic mirror, a central normal to said mirror being inclined at one-half the included angle between the telescope axis and the laser-radiation axis, said optical means being such in conjunction with the refractive power of the inspected eye as to focus a single spot of laser radiation on the telescope axis and at a posterior region of the eye, centrally of the illuminated field of inspection, said optical means including an indexible carrier of lens elements of different corrective power, and means for selectively indexing said lens elements into and out of the laser-radiation axis for correctively offsetting refractive error of the inspected eye and for selecting a prospective laser coagulation of predetermined size on an internal structure of the inspected eye.

2. The system of claim 1, in which said optical means includes first lens means converting cable-exit radiation to a collimated beam, said lens elements being selectively indexible with respect to said collimated beam.

3. The system of claim 1, in which said indexible carrier of lens elements is within said housing, and in which said means for selectively indexing said lens elements is accessible externally of said housing.

4. The system of claim 1, in which said telescope is monocular and includes reticle means indicating the instantaneous impingement of the telescope-viewing axis within the illuminated field of said light source.

5. The system of claim 1, in which said dichroic mirror is selected (a) for its spectral character to reflect substantially only a narrow band which includes the laser-radiation wavelength and (b) for its ability to transmit visible light outside said narrow band.

6. The system of claim 5, in which said laser is an argon laser and said narrow band includes 488-nm and 514-nm.

7. The system of claim 5, in which said laser is an argon laser and said narrow band includes 514-nm to the exclusion of shorter wavelengths such as 488-nm.

8. The system of claim 5, in which said laser is a frequency-doubled neodymium-YAG laser and said narrow band includes 532-nm.

9. The system of claim 5, in which said laser is a krypton laser and said narrow band includes 647.1-nm.

10. The system of claim 5, in which said mirror has a reflection coefficient of about 90 percent within said narrow band.

11. The system of claim 1, in which shutter means at the output of said laser means is interposed between laser-beam output and the coupling to said optical-fiber cable, and selectively operable shutter-control means including a flexible connection to said shutter.

12. The system of claim 11, in which said control means includes a foot-operated switch.

13. The system of claim 11, in which said control means includes a switch mounted to said housing.

14. The system of claim 11, in which said housing includes a hand-grip portion extending in one direction of generally radially projecting offset from the telescope axis, and in which said switch is mounted to said hand-grip portion.

15. The system of claim 11, in which said shutter is of a variety passing a very small fraction of the laser-beam output when in closed position, said fraction being in the order of one or two percent.

16. The system of claim 11, in which said shutter includes selectively operable means whereby exposure time can be preselected and in which, if desired, the opening and the closing of the shutter may each be via separate operator actuations of said control means.

17. The system of claim 1, in which a detachable coupling retains the cable at said housing.

18. A portable indirect photocoagulation delivery system, comprising in combination, a hand-held ophthalmoscope including a low-power afocal telescope comprising a housing and optical elements that can be focused to inspect the interior of an eye, a light source carried by said housing and means including a beam splitter on the telescope axis for projecting light over an illuminated central field region of inspection of the interior of the eye; laser means having a radiation-beam output in a portion of the visible spectrum, means including an elongate flexible optical-fiber cable coupled at one end to said output, said housing having a side port and retaining the other end of said cable through said side port and directing cable output on a laser-radiation axis within said housing; beam-splitting means carried by said housing and in the path of telescope viewing, optical means on the laser-radiation axis directing said laser-radiation axis to intersect the telescope axis at said beam-splitting means, a central normal to said mirror being inclined at one-half the included angle between the telescope axis and the laser-radiation axis, said optical means being such in conjunction with the refractive power of the eye as to focus a single spot of laser radiation on the telescope axis and at a posterior region of the eye, centrally of the illuminated field of inspection, said telescope including a filter on the viewing side of said beam-splitting means and characterized by a narrow band of attenuation which includes the radiation frequency of said laser means, said optical means including an indexible carrier of lens elements of different corrective power, and means for selectively indexing said lens elements into and out of the laser-radiation axis for correctively offsetting refractive error of the eye and for selecting a prospective laser coagulation of predetermined size on an internal structure of the eye.

19. As an article of manufacture, a photocoagulation delivery system adapted for assembly to a hand-held ophthalmoscope with a body having an objective-lens port on a monocular-viewing axis, said delivery system comprising an accessory body adapted for assembly to the ophthalmoscope body at the objective-lens port, whereby when thus assembled the combined ophthalmoscope and accessory body constitute a single hand-held instrument, said accessory body having a side port adapted to retain the output end of an optical-fiber cable on an injection axis intersecting the monocular-viewing axis adjacent the objective-lens port, and a dichroic mirror carried by said accessory body, the central normal to said mirror being inclined at one-half the included angle between the monocular-viewing axis and the injection axis, said optical-fiber cable being selected for compatible transmission of the output of a selected laser, the dichroic mirror being selected (a) for its special character to reflect substantially only a narrow band which includes the laser-radiation wavelength and (b) for its ability to transmit visible light outside said narrow band, said optical means including an indexible carrier of lens elements of different corrective power, and means for selectively indexing said lens elements into and out of the laser-radiation axis for correctively offsetting refractive error of the eye and for selecting a prospective laser coagulation of predetermined size on an internal structure of the eye.

* * * * *